United States Patent [19]

Ueno et al.

[11] Patent Number: 4,592,892

[45] Date of Patent: Jun. 3, 1986

[54] AQUEOUS STERILIZING AGENT FOR FOODS OR FOOD PROCESSING MACHINES AND UTENSILS

[75] Inventors: Ryuzo Ueno, Nishinomiya; Toshio Matsuda, Itami; Tatsuo Kanayama, Takarazuka; Munemitsu Yamamoto; Ryoichi Hitotsuya, both of Nishinomiya, all of Japan

[73] Assignee: Kabushiki Kaisha Ueno Seiyaku Oyo Kenkyujo, Osaka, Japan

[21] Appl. No.: 439,904

[22] Filed: Nov. 8, 1982

[30] Foreign Application Priority Data

Nov. 12, 1981 [JP] Japan .................................. 56-180332
Jul. 23, 1982 [JP] Japan .................................. 57-127644

[51] Int. Cl.$^4$ ...................... A01N 59/26; A23L 3/34; A61L 2/18
[52] U.S. Cl. ................... 422/28; 252/174.14; 424/128; 426/521; 514/724
[58] Field of Search ................... 422/13, 28, 32; 134/25.3; 426/506, 521; 423/312, 421; 252/174.14; 424/127, 128, 343

[56] References Cited

U.S. PATENT DOCUMENTS

| | | | |
|---|---|---|---|
| 3,036,923 | 5/1962 | Mahon et al. | 426/506 |
| 3,410,804 | 11/1968 | Walsh | 423/312 X |
| 3,440,054 | 4/1969 | Sair | 426/506 X |
| 3,746,553 | 7/1973 | Anderson | 134/25.3 X |
| 3,798,331 | 3/1974 | Bavisotto et al. | 426/521 X |
| 3,885,050 | 5/1975 | Ridgeway et al. | 426/521 X |
| 3,892,875 | 7/1975 | Steir | 426/506 X |
| 3,898,186 | 8/1975 | Mermelstein et al. | 252/174.23 |
| 3,908,031 | 9/1975 | Wistreich et al. | 426/521 X |
| 3,912,450 | 10/1975 | Boucher | 422/20 |
| 4,081,395 | 3/1978 | Talley | 252/106 |
| 4,165,375 | 8/1979 | Berger et al. | 424/263 |
| 4,241,014 | 12/1980 | Hirozawa et al. | 422/13 |
| 4,276,263 | 6/1981 | Anderson et al. | 422/37 X |
| 4,284,599 | 8/1981 | Anderson et al. | 422/37 X |
| 4,342,790 | 8/1982 | Katoh et al. | 426/506 X |

FOREIGN PATENT DOCUMENTS

| | | | |
|---|---|---|---|
| 0067778 | 12/1974 | Japan | 426/521 |
| 0089478 | 12/1978 | Japan | 422/13 |
| 1339503 | 12/1973 | United Kingdom . | |

OTHER PUBLICATIONS

The Condensed Chemical Dictionary; Ed. Gessner G. Hanley; Van Nostrand Reinhold Co.; 1981; pp. 423, 846, 853, 930, 949.

Primary Examiner—Barry S. Richman
Assistant Examiner—Brion P. Heaney
Attorney, Agent, or Firm—Sherman and Shalloway

[57] ABSTRACT

An aqueous sterilizing agent for foods or food processing machines and utensils, comprising an aqueous solution containing about 0.5 to 75% by weight ethanol, an alkali carbonate selected from the group consisting of sodium carbonate and potassium carbonate and a trialkali phosphate selected from the group consisting of trisodium phosphate and tripotassium phosphate wherein the combined amount of the carbonate and phosphate is about 0.5 to 40% by weight; and a method of sterilizing foods or food processing machines and utensils, which comprises contacting the foods or food processing machines and utensils with the above aqueous sterilizing agent.

34 Claims, No Drawings

AQUEOUS STERILIZING AGENT FOR FOODS OR FOOD PROCESSING MACHINES AND UTENSILS

This invention relates to an aqueous sterilizing agent for foods or food processing machines and utensils, and to a method for sterilizing foods for food processing machines and utensils by using the aqueous sterilizing agent.

In recent years, a variety of foods are processed in quantities in certain specified areas and transported to various places of consumption. Hence, periods of time which elapse for transportation from the places of production to consumers and before the foods are cooked and eaten by the consumers are prolonged, and food poisoning and spoilage by microorganisms frequently occur.

Microbial contamination which causes food poisoning and spoilage is attributed to raw materials for foods and to the handling of such materials or foods during processing, transportation and sales. For example, fish paste products, hams and sausages are said to be highly safe foods because they undergo heat-treatment during processing. In these foods, too, secondary contamination becomes a problem during the time between heat-treatment and packaging. In order, therefore, to prevent food poisoning and spoilage, it is important to prevent secondary contamination during the processing of these highly safe foods as well as foods having a low degree of safety.

Ready-to-eat or ready-to-cook foods such as vegetable salads, Chinese dishes, hamburger steak, and meat balls have shown a rapidly increasing demand on the market in Japan, and an especially great demand has been noted for salads which use much raw vegetables. Frequently, vegetables for salads, such as cucumber, tomato, cabbage, Chinese cabbage, onion and celery are liable to be subjected to strong contamination by coliform bacteria.

There is also a problem of contamination by food-poisoning bacteria, particularly bacteria of the genus Salmonella, present in the human body (working personnel in food processing factories, and cooks), fishes and shells, chickens and chicken eggs. In order to prevent food spoilage and poisoning which occur as a result of microbial contamination of foods, a method of sterilizing foods themselves, or machines and utensils with which the foods make contact has been investigated in addition to a method of adding antiseptically effective substances to foods. For example, contaminating bacteria on vegetables are now removed by a blanching method. This method, however, has the defect that because the vegetables are dipped in a blanching liquor at high temperatures, the vegetable tissues will be thermally degraded and their flavors will be markedly reduced. Hydrogen peroxide at effective concentrations has a high sterilizing effect with reduced degrading effects on foods, but its reported carcinogenicity has limited its application to foods. On the other hand, an attempt has been made at a method of removing bacteria using an aqueous solution of sodium hypochlorite (by dipping, spraying, etc.). The bacteria-removing effect is not sufficient when the concentration of available chlorine is less than 200 ppm, and a smell of chlorine remains when the concentration is 200 ppm or more. The corrosion of the machines and utensils by chlorine also gives rise to a problem. In addition, it has recently been reported that the reaction of chlorine with an organic material may result in the formation of a carcinogenic substance.

In some food processing factories, investigations have been undertaken about the killing of bacteria and fungi which cause food poisoning and spoilage by spraying ethanol onto foods or dipping foods in ethanol. This method, however, has the disadvantage that at the effective concentrations of 70 to 75%, the smell of ethanol is strong and markedly impairs the flavors of foods, and that ethanol will denature proteins and cause a degradation in quality and discoloration. In addition, since ethanol is flammable, rigorous standards are imposed on it by the Fire Prevention Regulations and its handling is troublesome.

Aqueous solutions of organic acids such as acetic acid and lactic acid in high concentrations have a sterilizing power. However, they have a sour taste and an acidic smell, and greatly affect the quality of foods, resulting in discoloration, hardening of textures, etc. They are also unsuitable as sterilizing agents for food processing machines and utensils because their peculiar irritating smell adversely affects the working environment.

Thus, in spite of the fact that the removal and killing of noxious microorganisms on foods and food processing machines and utensils is very important in food hygiene and food processing, no effective measure has been established as yet.

It is an object of this invention to provide a sterilizing agent for foods and food processing machines and utensils, which has a reduced toxicity and a high degree of safety, does not reduce the flavors and qualities of foods, and does not impair the environment in which foods are processed.

Various investigations of the present inventors have led to the discovery that a combination of ethanol with at least one alkaline substance gives an excellent synergistic effect, and can control contaminating bacteria at much lower concentrations than those which are necessary when they are used individually.

The present inventors have found that an alkali carbonate greatly increases the solubility of a trialkali phosphate; that these compounds increase the durability of the sterilizing effect; and that an especially excellent synergistic effect is obtained by conjointly using ethanol and these two alkaline substances.

Thus, according to this invention, there is provided an aqueous sterilizing agent for foods and food processing machines and utensils, which comprises ethanol and at least one alkaline substance as active ingredients.

Illustrative of the alkaline substance used in this invention are alkali hydroxides, alkali carbonates, alkali bicarbonates, trialkali phosphates, dialkali phosphates, alkali polyphosphates and alkali salts of organic acids. Examples are alkali metal salts such as sodium or potassium salts, and alkaline earth metal salts such as calcium and magnesium salts. Sodium citrate, sodium tartrate, sodium lactate and sodium acetate are also suitable. A small amount of an acidic substance or a neutral or nearly neutral organic or inorganic acid salt may be added in amounts which do not cause the disappearance of the alkalinity of the alkaline substances. If desired, known antimicrobial substances may be added in amounts which do not render them ineffective.

The aqueous sterilizing agent of this invention may further contain a small amount of a polyhydric alcohol such as propylene glycol and glycerol.

The aqueous sterilizing agent of this invention is used either as such, or as required after diluting it properly with water. Preferably, during use, the aqueous sterilizing agent of the invention contains 0.5 to 75 wt% of ethanol and 0.005 to 40 wt% of the alkaline substances (in the anhydrous state). By contact of the aqueous sterilizing agent at these concentrations, most microorganisms can be killed within 30 seconds. For practical purposes, it is preferred to maintain the contact for 30 seconds to 30 minutes. Contacting for more than 30 minutes does not reduce the flavors and qualities of foods, nor does it give rise to any problem in the safety of foods, the safety of operations in factories, etc., and the corrosion of food processing machines and utensils.

The pH of the aqueous sterilizing agent of this invention is at least 10.0 during use.

In a preferred embodiment, the sterilizing agent of this invention comprises ethanol, an alkali carbonate and a trialkali phosphate as active ingredients.

Preferred alkali carbonates are anhydrous or hydrous potassium carbonate and sodium carbonate. Preferred trialkali phosphates are anhydrous or hydrous trisodium phosphate and tripotassium phosphate. Because a combination of potassium carbonate with trisodium phosphate and a combination of an alkali carbonate with tripotassium phosphate bring about a great increase in solubility of the trialkali phosphate, they readily enable the use of trisodium phosphate. It is also easy to use trisodium phosphate crystals which are available as pure products, but are difficult to dissolve at low temperatures.

In addition to ethanol and the two alkali components, another neutral or alkaline substance, a known antimicrobial agent, etc. may be added further, if desired.

The present invention also provides a method for sterilizing foods or food processing machines and utensils, which comprises contacting an aqueous sterilizing agent comprising ethanol, an alkali carbonate and a trialkali phosphate as active ingredients, either as such or after being diluted suitably with water, with the foods or food processing machines and utensils.

In the process of this invention, it is preferred to use the aqueous sterilizing agent which contains 0.5 to 75% of ethanol and 0.005 to 40% of the alkaline substances (in the anhydrous state) as described hereinabove.

Sterilization in accordance with the method of this invention is carried out by contacting the aqueous sterilizing agent with foods or food processing machines and utensils.

Foods which can be sterilized by the method of this invention are primary processed foods, secondary processed foods, and raw materials or ready-to-process materials for these foods. Examples of these foods include fish and meat products such as "kamaboko", "narutomaki", "hampen", sausages, Vienna sausages, hams and bacons; raw vegetables such as cucumber, tomato, cabbage, onion, lettuce and celery; various kinds of noodles such as Chinese noodles, Japanese noodles, buckwheat noodles, Japanese fine noodles, spaghetti, macaronies; ready-to-eat or ready-to-cook foods such as vegetable salads, Chinese dishes, hamburger steaks, and meat balls; tofu; various fishes, meat, chicken, chicken eggs, seafoods, and semi-dried and dried products of seafoods. They may include these foods before or after refrigeration.

Examples of the food processing machines and utensils which can be sterilized in accordance with this invention are cooking plates, cooking knives, kitchenware, cloths, agitators, mixers, homogenizers, automatic cutters, slicers, carrying receptacles, packaging receptacles, and various other machines and utensils with which foods make contact.

Noxious microorganisms adhering to the human body can also be skilled when the working personnel in food processing factories and cooks dip their hands in the aqueous sterilizing agent of this invention or wipe their hands with adsorbent cotton or gauzes impregnated with the aqueous sterilizing agent of the invention.

By using the aqueous sterilizing agent of this invention, food poisoning is prevented, and the preservability of processed foods is maintained for an extended period of time with their spoilage being greatly inhibited.

Using *Escherichia coli* NIHJ JC-2, a food-poisoning bacterium and the most important contamination indicating bacterium in food hygiene, effective combinations of ingredients of the sterilizing agent were examined in vitro (Test Examples 1 to 3). Using sterilizing preparations prepared on the basis of the results of Test Examples 1 to 3 (Preparation Examples 1 to 10), the sterilizing effects of these preparations in foods were examined (Examples 1 to 10). In each of these examples, parts and percentage are by weight.

TEST EXAMPLE 1

(a) The following experiment was conducted in order to examine the sterilizing effect of a combination of ethanol with an alkaline substance.

*Escherichia coli* NIHJ JC-2 was inoculated in a brain heart infusion broth (BHI), and cultivated at 37° C. for 24 hours. The culture was diluted to 1:10 with a sterilized physiological saline and the resulting *Escherichia coli* was used as a test bacterial suspension.

Sodium hydroxide, sodium carbonate, trisodium phosphate 12-hydrate, sodium pyrophosphate, sodium tripolyphosphate and sodium bicarbonate were used as the alkaline substance.

One milliliter of the test bacterial suspension was mixed with 9 ml of a test agent prepared by adding sterilized water to ethanol and each of the various alkaline substances so that the concentrations of these compounds became 10/9 of their predetermined concentrations. The mixture was maintained at 20° C. for 30 seconds. Then, one loopful of the mixture was inoculated in a fresh liquid medium and cultivated at 37° C. for 48 hours.

The presence or absence of bacterial growth in the culture medium was observed with unaided eyes. When no bacterial growth was observed, it was evaluated as "complete sterilization possible" (−), and when bacterial growth was observed, it was evaluated as "sterilization impossible" (+). The concentration of the agent required for complete sterilization was measured in each case.

The results are shown in Table 1. It is seen from Table 1 that the conjoint use of ethanol and the alkaline substance produced a synergisic effect, and this effect was particularly remarkable in the case of using ethanol in combination with sodium carbonate or trisodium phosphate.

TABLE 1

| Type and concentration (in the anhydrous state, wt. %) of the alkaline substance | | Concentration of ethanol (%) | | | | | |
|---|---|---|---|---|---|---|---|
| | | 40 | 30 | 20 | 15 | 10 | 5 | 0 |
| Sodium carbonate | 10 | | | − | − | − | + | + |
| | 7 | | | − | − | − | + | + |

TABLE 1-continued

| Type and concentration (in the anhydrous state, wt. %) of the alkaline substance | | Concentration of ethanol (%) | | | | | | |
|---|---|---|---|---|---|---|---|---|
| | | 40 | 30 | 20 | 15 | 10 | 5 | 0 |
| | 5 | | | − | − | − | + | + |
| | 3 | | −. | − | − | + | + | + |
| | 1 | − | + | + | + | + | + | + |
| | 0 | − | + | + | + | + | + | + |
| Trisodium phosphate | 1 | − | − | − | − | − | − | − |
| | 0.5 | − | − | − | − | − | − | + |
| | 0.25 | − | − | − | − | − | + | + |
| | 0.125 | − | − | − | − | + | + | + |
| | 0.06 | − | − | − | + | + | + | + |
| | 0 | − | + | + | + | + | + | + |
| Sodium pyrophosphate | 4 | | | | | | + | + |
| | 2 | | + | + | + | + | + | + |
| | 1 | | + | + | + | + | + | + |
| | 0.5 | − | − | + | + | + | + | + |
| | 0 | − | + | + | + | + | + | + |
| Sodium tripolyphosphate | 4 | | | + | + | + | + | + |
| | 2 | | | + | + | + | + | + |
| | 1 | | | + | + | + | + | + |
| | 0.5 | − | − | + | + | + | + | + |
| | 0 | − | + | + | + | + | + | + |
| Sodium hydrogen carbonate | 4 | | − | + | + | + | + | + |
| | 2 | | − | + | + | + | + | + |
| | 1 | − | − | + | + | + | + | + |
| | 0.5 | − | − | + | + | + | + | + |
| | 0 | − | + | + | + | + | + | + |
| Sodium hydroxide | 0.2 | − | − | − | − | − | − | + |
| | 0.1 | − | − | − | − | − | − | + |
| | 0.07 | − | − | − | − | − | + | + |
| | 0.05 | − | − | − | + | + | + | + |
| | 0.02 | − | − | − | + | + | + | + |
| | 0 | − | + | + | + | + | + | + |

Note:
Where there is no mark of + or −, no experiment was conducted.

(b) The sterilizing effect of an agent consisting of ethanol, sodium carbonate and trisodium phosphate 12-hydrate was measured in the same way as in experiment (a) (the contacting time 30 seconds).

The results are shown in Table 2. It is seen from Table 2 that when the three ingredients were used, a stronger sterilizing effect (synergistic effect) was noted than that which would be expected from the conjoint use of ethanol and sodium carbonate, or the conjoint use of ethanol and trisodium phosphate.

TABLE 2

| Concentration of trisodium phosphate (wt. % in the anhydrous state) (%) | Concentration of sodium carbonate (%) | Concentration of ethanol (%) | | | | | | | |
|---|---|---|---|---|---|---|---|---|---|
| | | 40 | 30 | 20 | 15 | 10 | 7 | 5 | 0 |
| 0 | 5 | | | − | − | − | + | + | + |
| | 3 | | − | − | − | + | + | + | + |
| | 2 | − | − | + | + | + | + | + | + |
| | 1 | − | + | + | + | + | + | + | + |
| | 0.5 | − | + | + | + | + | + | + | + |
| | 0 | − | + | + | + | + | + | + | + |
| 0.05 | 5 | | | − | − | − | + | + | + |
| | 3 | | | − | − | − | + | + | + |
| | 2 | − | − | − | − | + | + | + | + |
| | 1 | − | − | − | − | + | + | + | + |
| | 0.5 | − | − | − | − | + | + | + | + |
| | 0 | − | − | + | + | + | + | + | + |
| 0.1 | 5 | | | − | − | − | − | + | + |
| | 3 | | | − | − | − | − | + | + |
| | 2 | | | − | − | − | + | + | + |
| | 1 | − | − | − | − | + | + | + | + |
| | 0.5 | − | − | − | − | + | + | + | + |
| | 0 | − | − | − | + | + | + | + | + |
| 0.2 | 5 | | | − | − | − | − | − | + |
| | 3 | | | − | − | − | − | − | + |
| | 2 | | | − | − | − | − | + | + |
| | 1 | − | − | − | − | − | − | + | + |
| | 0.5 | − | − | − | − | − | − | + | + |
| | 0 | − | − | − | − | + | + | + | + |

Note:
Where there is no mark of + or −, no experiment was conducted.

It can be seen from these experimental results that the conjoint use of ethanol and the alkaline substance, especially the conjoint use of three ingredients, ethanol, sodium carbonate and trisodium phosphate, can markedly reduce the required concentrations of the individual ingredients.

TEST EXAMPLE 2

The sterilizing effect of a combination of ethanol, potassium carbonate and trisodium phosphate 12-hydrate was examined in the same way as in Test Example 1.

The results are shown in Table 3. It is seen from the results shown in Table 3 that the use of the three ingredients in combination produced a much stronger synergistic sterilizing effect than could be expected from the conjoint use of ethanol and potassium carbonate or the conjoint use of ethanol and trisodium phosphate, and could markedly reduce the required concentrations of the individual ingredients.

TABLE 3

| Potassium carbonate (%) | Trisodium phosphate (wt. % in the anhydrous state) (%) | Concentration of ethanol (%) | | | | | | | |
|---|---|---|---|---|---|---|---|---|---|
| | | 40 | 30 | 20 | 15 | 10 | 5 | 3 | 0 |
| 0 | 0 | − | + | + | + | + | + | + | + |
| | 0.05 | − | − | + | + | + | + | + | + |
| | 0.1 | − | − | − | + | + | + | + | + |
| | 0.2 | − | − | − | − | + | + | + | + |
| 0.5 | 0 | − | + | + | + | + | + | + | + |
| | 0.05 | − | − | − | − | + | + | + | + |
| | 0.1 | − | − | − | − | − | + | + | + |
| | 0.2 | − | − | − | − | − | − | + | + |
| 1 | 0 | − | − | + | + | + | + | + | + |
| | 0.05 | − | − | − | − | + | + | + | + |
| | 0.1 | − | − | − | − | − | + | + | + |
| | 0.2 | − | − | − | − | − | − | − | + |
| 2 | 0 | − | − | + | + | + | + | + | + |
| | 0.05 | − | − | − | + | + | + | + | + |
| | 0.1 | − | − | − | − | − | + | + | + |
| | 0.2 | − | − | − | − | − | − | − | + |
| 3 | 0 | | − | − | − | + | + | + | + |
| | 0.05 | | − | − | − | − | − | + | + |
| | 0.1 | | − | − | − | − | − | + | + |
| | 0.2 | | − | − | − | − | − | − | + |
| 5 | 0 | | | − | − | + | + | + | + |
| | 0.05 | | | − | − | − | − | + | + |
| | 0.1 | | | − | − | − | − | − | + |
| | 0.2 | | | − | − | − | − | − | + |

TEST EXAMPLE 3

Aqueous solutions containing ethanol, trisodium phosphate 12-hydrate and potassium carbonate in the concentrations shown in Table 4 were each stored at −5° C. for 3 days, and the solubility of trisodium phosphate was examined by the presence or absence of a precipitate. The results are shown in Table 4. It is seen from the results that potassium carbonate markedly increases the solubility of trisodium phosphate.

TABLE 4

| Trisodium phosphate (wt. % in the anhydrous state) | Potassium carbonate (%) | Ethanol (%) | | | | | |
|---|---|---|---|---|---|---|---|
| | | 0 | 1 | 3 | 5 | 7 | 9 | 10 |
| 4 | 0 | + | | | + | | | |
| 5 | 10 | − | − | − | | | | |
| 6 | 12 | − | − | − | | | | |
| 7 | 14 | − | − | − | | | | |
| 8 | 16 | − | − | − | | | | |
| 9 | 18 | − | − | − | | | | |
| 10 | 20 | − | − | − | − | − | − | + |
| 11 | 22 | − | − | − | − | | | |
| 11 | 24 | − | − | − | − | | | |
| 11 | 26 | − | − | − | − | | | |
| 12 | 28 | − | − | − | +* | | | |
| 15 | 30 | + | | | | | | |

Note:
− shows dissolution, and +, formation of a precipitate. The blanks show that no test was conducted. The asterisk showed that two layer separation occurred.

PREPARATION EXAMPLE 1

A suitable amount of water was added to a mixture consisting of 6.1 parts of ethanol standardized in Japanese Pharmacopoeia, 2 parts of trisodium phosphate (12-hydrate) and 4 parts of sodium carbonate to prepare 100 parts of a solution.

PREPARATION EXAMPLE 2

A suitable amount of water was added to a mixture consisting of 8.7 parts of ethanol standardized in Japanese Pharmacopoeia, 1.7 parts of trisodium phosphate (12-hydrate) and 2 parts of sodium carbonate to prepare 100 parts of a solution.

PREPARATION EXAMPLE 3

A suitable amount of water was added to a mixture consisting of 8.7 parts of ethanol standardized in Japanese Pharmacopoeia and 5 parts of sodium carbonate to prepare 100 parts of a solution.

PREPARATION EXAMPLE 4

A suitable amount of water was added to a mixture consisting of 8.7 parts of ethanol standardized in Japanese Pharmacopoeia and 1.7 parts of trisodium phosphate (12-hydrate) to prepare 100 parts of a solution.

PREPARATION EXAMPLE 5

A suitable amount of water was added to a mixture consisting of 4.4 parts of ethanol standardized in Japanese Pharmacopoeia, 0.2 part of sodium hydroxide, 2 parts of sodium carbonate and 0.9 part of trisodium phosphate (12-hydrate) to prepare 100 parts of a solution.

PREPARATION EXAMPLE 6

Sodium hydroxide (0.2 part) was dissolved in 8.7 parts of ethanol standardized in Japanese Pharmacopoeia, and a suitable amount of water was added to the solution to adjust the total amount of the solution to 100 parts.

PREPARATION EXAMPLE 7

A suitable amount of water was added to a mixture consisting of 16 parts of ethanol standardized in Japanese Pharmacopoeia, 6 parts of potassium carbonate and 6 parts of trisodium phosphate (12-hydrate) to prepare 100 parts of a solution.

PREPARATION EXAMPLE 8

A suitable amount of water was added to a mixture consisting of 10 parts of ethanol standardized in Japanese Pharmacopoeia, 2 parts of sodium carbonate and 8 parts of tripotassium phosphate (anhydrous salt) to form 100 parts of a solution.

PREPARATION EXAMPLE 9

A suitable amount of water was added to a mixture consisting of 10 parts of ethanol standardized in Japanese Pharmacopoeia, 4 parts of potassium carbonate and 4 parts of tripotassium phosphate (anhydrous salt) to prepare 100 parts of a solution.

PREPARATION EXAMPLE 10

A suitable amount of water was added to a mixture consisting of 5 parts of ethanol standardized in Japanese Pharmacopoeia, 10 parts of trisodium phosphate (anhydrous salt) and 20 parts of potassium carbonate to prepare 100 parts of a solution.

EXAMPLE 1

The sterilizing effect of a mixture of 7% ethanol, 4.0–1.0% sodium carbonate and 2.0–0.5% trisodium phosphate (12-hydrate) was examined on broilers whose contamination with bacteria of the genus Salmonella particularly causes a problem.

About 50 g of the flesh taken from near the wing of a broiler was dipped for 30 seconds in a suspension of *Salmonella typhimurium* ATCC 14028, then withdrawn, and left to stand for 5 minutes to permit sufficient adhesion of the bacteria.

Then, the broiler flesh was dipped in the mixture of ethanol, sodium carbonate and trisodium phosphate (12-hydrate) at 5° C. for 1 minute and 5 minutes, respectively. Immediately then, it was withdrawn from the mixture, and the number of the Salmonella bacteria was measured by the MPN method (most probable number method) using an SBG basic culture medium.

For comparison, the measurement of the bacteria was made after the broiler flesh dipped in the bacterial suspension was then dipped in distilled water, a solution of sodium hypochlorite (available chlorine 200 ppm), and 70% ethanol, respectively.

The results are summarized in Table 5. The numerical figures in the table show the number of bacteria (cells/g).

TABLE 5

| wt. % of trisodium phosphate (as anhydrous salt) | Dipping time (min.) | Sodium carbonate (%) | | | | |
|---|---|---|---|---|---|---|
| | | 4 | 3 | 2 | 1 | 0 |
| 5 | 1 | 0 | 0 | 0 | 0 | 0 |
| | 5 | 0 | 0 | 0 | 0 | 0 |
| 2.5 | 1 | 0 | 0 | 0 | $1.15 \times 10^2$ | $1.2 \times 10^3$ |
| | 5 | 0 | 0 | 0 | 0 | $1.2 \times 10^2$ |

TABLE 5-continued

| wt. % of trisodium phosphate (as anhydrous salt) | Dipping time (min.) | Sodium carbonate (%) | | | | |
|---|---|---|---|---|---|---|
| | | 4 | 3 | 2 | 1 | 0 |
| 1 | 1 | 0 | 0 | 0 | $\geq 1.2 \times 10^3$ | $\geq 1.2 \times 10^3$ |
| | 5 | 0 | 0 | 0 | 0 | $4.65 \times 10$ |
| 0.5 | 1 | 0 | 0 | $4.65 \times 10^2$ | $\geq 1.2 \times 10^3$ | $\geq 1.2 \times 10^3$ |
| | 5 | 0 | 0 | 0 | $4.65 \times 10$ | $1.15 \times 10$ |
| 0 | 1 | 0 | $1.2 \times 10^2$ | $\geq 1.2 \times 10^3$ | $\geq 1.2 \times 10^3$ | $\geq 1.2 \times 10^3$ |
| | 5 | 0 | $4.65 \times 10$ | $1.15 \times 10^2$ | $1.2 \times 10^3$ | $1.2 \times 10^3$ |
| Sodium hypochlorite | 5 | | | $5.5 \times 10^3$ | | |
| 70% ethanol | 5 | | | $5.5 \times 10$ | | |
| Distilled water | 5 | | | $5.5 \times 10^4$ | | |

It is seen from the results that by using the mixture of 7% ethanol and 2.5-4.0% sodium carbonate and/or 0.5-10% trisodium phosphate (12-hydrate), the presence of the Salmonella bacteria can be made negative within 1 minute and this sterilizing effect is much stronger than sodium hypochlorite (available chlorine 200 ppm) or 70% ethanol.

When the contaminated broiler flesh was dipped in the above chemical for 5 minutes, all the test lots showed a sterilizing effect of at least 90%.

EXAMPLE 2

(a) The sterilizing effects of the solution obtained in Preparation Example 1, a 4:3 dilution thereof, a 2:1 dilution thereof, a 4:1 dilution thereof, and as a comparison, a sodium hypochlorite solution (available chlorine 200 ppm) were examined on the flesh taken from near the wing of a broiler inoculated with Salmonella bacteria in the same way as in Example 1.

The results are shown in Table 6.

The following conclusions can be drawn from the data given in Table 6.

When the broiler flesh is dipped for 1 minute in the solution of Preparation Example 1 and its 4:3 dilution, the Salmonella bacteria can be completely killed.

With the 2:1 dilution, the presence of the Salmonella bacteria becomes negative when the contaminated broiler flesh was dipped in it for 3 minutes.

With the 4:1 dilution, too, when the contaminated broiler flesh is dipped in it for more than 3 minutes, the number of Salmonella bacterial cells decreases to below $10^3$/g.

Thus, the solution obtained in Preparation Example 1 and its dilutions have sufficient sterilizing effects for practical purposes.

TABLE 6

| Chemicals | Time (minutes) | | | |
|---|---|---|---|---|
| | 1 | 3 | 5 | 10 |
| Distilled water | | | | $1.5 \times 10^4$ |
| Sodium hypochlorite | | | | $4.65 \times 10^3$ |
| Solution of Preparation Example 1 | 0 | 0 | 0 | 0 |
| 4:3 dilution | 0 | 0 | 0 | 0 |
| 2:1 dilution | $1.2 \times 10^2$ | 0 | 0 | 0 |
| 4:1 dilution | $\geq 1.2 \times 10^3$ | $5.5 \times 10^2$ | $2.3 \times 10^2$ | $2.3 \times 10^2$ |

(b) In order to examine the effect of the aqueous sterilizing agent of this invention in the quality, especially the flavor, of foods, the flesh taken from the breast of chicken was dipped for 5 minutes in the same chemicals as used in (a) above. The appearance and smell of the flesh of chicken immediately after dipping, and the appearance, taste and smell of the chicken after grilling on a hot plate were organoleptically evaluated by a panel of 10 specialists.

The results are shown in Table 7. It is seen from Table 7 that the aqueous sterilizing agent of this invention does not at all affect the flavor of foods even when it is used without dilution.

The aqueous sterilizing agent of this invention was also effective for killing noxious microorganisms, coliform bacteria, staphylococcal bacteria, and Salmonella bacteria on beef, pork and raw seafoods (such as shelled shrimps) as well as on chicken.

TABLE 7

| Chemicals | Immediately after dipping | | After heating on a hot plate | | |
|---|---|---|---|---|---|
| | Appearance | Smell | Appearance | Smell | Taste |
| Distilled water | 0 | 0 | 0 | 0 | 0 |
| Sodium hypochlorite | 3 | 10 | 0 | 2 | 0 |
| Solution of Preparation Example 1 | 0 | 0 | 0 | 0 | 0 |
| 4:3 dilution | 0 | 0 | 0 | 0 | 0 |
| 2:1 dilution | 0 | 0 | 0 | 0 | 0 |
| 4:1 dilution | 0 | 0 | 0 | 0 | 0 |

Note:
The figures in the table indicate the number of panelists who detected a change in appearance, an unusual taste, or an unusual smell.

EXAMPLE 3

About 100 g of cucumber whose bacterial contamination is most troublesome among vegetables to be eaten raw was dipped for 15 minutes or 30 minutes in a 2:1 dilution of the solution prepared in Preparation Example 1, a 3.3:1 dilution thereof, a 10:1 dilution thereof, and a sodium hypochlorite solution (available chlorine 200 ppm), respectively. The cucumber was then withdrawn, homogenized in a customary manner, and then the number of bacterial cells was measured by the plate counter agar method. The number of general bacteria was measured by using a standard agar medium, and the number of coliform bacteria, by using a desoxycholate agar medium.

The results are shown in Table 8. It is seen from Table 8 that with the 2:1 and 3.3:1 dilutions of the solution prepared in Preparation Example 1, complete sterilization of coliform bacteria is possible in 15 minutes, and with the 10:1 dilution, it is possible in 30 minutes, and that when the cucumber was dipped for 15 minutes in the 10:1 dilution, a sterilizing effect of 99% can be obtained.

TABLE 8

| Chemical | Dipping time (min.) | Number of general bacterial (cells/g) | Number of coliform bacteria (cells/g) |
| --- | --- | --- | --- |
| Distilled water | 30 | $6.5 \times 10^5$ | $2.4 \times 10^4$ |
| Sodium hypochlorite | 15 | $5.4 \times 10^5$ | $1.9 \times 10^4$ |
|  | 30 | $2.4 \times 10^5$ | $3.6 \times 10^3$ |
| 2:1 dilution of the solution of Preparation Example 1 | 15 | $1.11 \times 10^4$ | 0 |
|  | 30 | $1.36 \times 10^3$ | 0 |
| 3.3:1 dilution of the solution of Preparation Example 1 | 15 | $2.71 \times 10^4$ | 0 |
|  | | $3.51 \times 10^3$ | 0 |
| 10:1 dilution of the solution of Preparation Example 1 | 15 | $7.2 \times 10^4$ | $1.3 \times 10^2$ |
|  | 30 | $4.3 \times 10^4$ | 0 |

EXAMPLE 4

In the production line of a fish jelly product like crab leg meat, the floor of the production room, the belt conveyers, cutters, containers for the product and the packaging station, in which the number of general bacteria was $10^3$ to $10^5$ and the number of coliform bacteria was 10 to $10^3$, were sprayed with the solution prepared in preparation Example 1 or dipped in the solution, and then the bacteria were collected by a wiping method ($30 \times 30$ cm). The number of general bacteria alive was measured by using a standard agar medium, and the number of coliform bacteria was measured by using a desoxycholate agar medium.

By the above spraying or dipping treatment, the number of general bacteria was reduced to 10 to $10^2$, and the coliform bacteria were completely killed. It is seen therefore that the aqueous sterilizing agent of this invention is effective for the sterilization of the equipment and utensils in food processing factories.

EXAMPLE 5

The sterilizing effect of the sterilizing agent of this invention was examined on bacteria adhering to the surface of chicken eggs.

About 67 g of chicken eggs were dipped for 30 seconds in a suspension of *Salmonella typhimurium* ATCC 14028 to permit sufficient adhesion of the bacteria. Then, the eggs were dipped in each of the chemicals shown in Table 9 for 1 minute or 5 minutes. The surfaces of the dipped eggs were wiped, and the number of general bacteria and the number of Salmonella bacteria were measured.

The results are shown in Table 9. It is seen from Table 1 that with the solution prepared in Preparation Example 1 and its 4:3 dilution, complete sterilization is possible in 1 minute, and with the 2:1 dilution, it is possible in 5 minute. Accordingly, the aqueous sterilizing agent of this invention is very effective also for sterilizing chicken eggs.

TABLE 9

| Chemical | Dipping time (min.) | Number of general bacteria (cells/g) | Number of Salmonella bacteria (cells/g) |
| --- | --- | --- | --- |
| Distilled water | 5 | $7.1 \times 10^4$ | $5.5 \times 10^2$ |
| Sodium hypochlorite (available Cl 200 ppm) | 1 | $6.9 \times 10^4$ | $2.3 \times 10^2$ |
|  | 5 | $8.7 \times 10^3$ | $1.2 \times 10^2$ |
| Solution prepared in Preparation Example 1 | 1 | $5.1 \times 10^2$ | 0 |
|  | 5 | $3.9 \times 10$ | 0 |
| 4:3 dilution of the solution prepared in Preparation Example 1 | 1 | $7.32 \times 10^2$ | 0 |
|  | 5 | $4.12 \times 10^2$ | 0 |
| 2:1 dilution of the solution of Preparation Example 1 | 1 | $1.04 \times 10^4$ | |
|  | 5 | $7.86 \times 10^3$ | 0 |
| 4:1 dilution of the solution prepared in Preparation Example 1 | 1 | $3.51 \times 10^4$ | $1.05 \times 10^2$ |
|  | 5 | $2.06 \times 10^4$ | $5.5 \times 10$ |

EXAMPLE 6

The sterilizing effects of the solutions prepared in preparation Examples 2 to 6 were examined on the flesh taken from near the wing of a broiler inoculated with Salmonella bacteria ($10^4$ cells per gram). With any of these solutions, the presence of the Salmonella bacteria could be made completely negative by dipping for 5 minutes.

Tuna was dipped for 1 to 5 minutes in each of the aforesaid solutions, and bacteria on the surface were examined by a wiping method. The presence of coliform bacteria, Salmonella bacteria and staphylococcal bacteria was not observed.

EXAMPLE 7

The surface skin of cuttlefish was removed, and the flesh was cut to pieces each weighing about 20 g. Five such pieces of cuttlefish to be eaten raw were dipped in 1 liter of each of the solutions indicated below for a predetermined time. After removing water, the sterilizing effects of these solutions on coliform bacteria and general bacteria were examined on the raw cuttlefish pieces.

As dipping solutions in accordance with this invention, a solution containing 15% ethanol, 6% potassium carbonate and 2.6% trisodium phosphate, its 4:3 dilution, and its 2:1 dilution were used. As a control, water was used as the dipping solution.

90 ml of sterilized physiological saline was added to 10 g of the sample, and the mixture was subjected to a Stomacker (laboratory blender) for 30 seconds. The sample was cultivated in a desoxycholate agar medium at 37° C. for 20 hours, and the number of coliform bacteria after the cultivation was examined. On the other hand, the sample was cultivated in a BGLB medium at 37° C. for 48 hours, and after the cultivation, the generation of gases was examined. The number of general bacteria was measured after cultivation at 37° C. for 48 hours in a standard agar medium.

The results are shown in Table 10. It is seen from the data given in Table 10 that coliform bacteria adhering to raw and fresh foods, especially fish for eating raw, can be killed by dipping for 1 to 5 minutes in the dipping solutions in accordance with this invention.

Organoleptic examination showed that the texture, palate, taste and smell of the raw cuttlefish were good.

TABLE 10

| Test lot | | Coliform bacteria | | | | | | Number of general bacteria Dipping time (min.) | | |
|---|---|---|---|---|---|---|---|---|---|---|
| | | Desoxycholate medium Dipping time (min.) | | | BGLB medium Dipping time (min.) | | | | | |
| | | 1 | 3 | 5 | 1 | 3 | 5 | 1 | 3 | 5 |
| Invention | Solution without dilution | — | — | — | —* | — | — | $1.2 \times 10^3$ | $8.5 \times 10^2$ | $1.7 \times 10^3$ |
| | 4:3 dilution | — | — | — | — | — | — | $3.4 \times 10^3$ | $2.4 \times 10^3$ | $3.6 \times 10^3$ |
| | 2:1 dilution | $2.0 \times 10$ | — | — | + | — | — | $2.6 \times 10^4$ | $1.3 \times 10^4$ | $5.8 \times 10^3$ |
| Control | Water | | $1.0 \times 10^2$ | | | + | | | | $2.6 \times 10^4$ |

*Generation of gases: — denotes no, and + denotes yes.

EXAMPLE 8

Bacteria were examined in the same way as in Example 7 on cut fleshes of Alaska pollack, broilers (round, flesh taken from near the wing, and parts meat), raw vegetables (cucumber, leek, parsley and lettuce), meats (beef, pork and sheep blocks), shrimps and lobsters (with or without shells), fish paste products ("chikuwa", "kamaboko", fried "kamaboko" and "naruto"), meat products (bacon, ham, Vienna sausage, salami sausage and Frankfurt sausage) and pork for raw ham (raw meat, meat after salting, meat after drying, and meat after smoking).

By dipping each of these foods for 30 seconds to 5 minutes in a dipping liquid prepared by diluting the dipping solution used in Example 7 to 10:3 to 1:1 (the vegetables were dipped in 100:6 dilution of the solution for 15 to 30 minutes), the coliform bacteria were completely killed. In raw meats, Salmonella bacteria were also killed.

EXAMPLE 9

Wheat flour (2.5 kg; 100 parts) were mixed with 0.6 parts of brine, 2 parts of common salt and 37 parts of water for 15 minutes. The mixture was rolled flat, and finely cut lengthwise. The noodles were steamed at 95° to 98° C. for 7 minutes and rapidly cooled in sterilized cold water. Four hundred grams of the resulting steamed Chinese noodles were dipped for 30 seconds in 1 liter of each of the dipping solutions shown in Table 11, and after removing water, divided into 40 g portions and packed in polyethylene bags. The bags were then heat-sealed.

Five out of the ten bags were steamed (reheated) at 85° C. for 30 minutes, and cooled. Both the reheated noodles and the non-reheated noodles were stored in a constant temperature vessel at 20° C. The appearance of the Chinese noodles was evaluated periodically, and the number of days (storage period) which elapsed until spoilage (generation of mold or softening by the bacterial effect) occurred in five bagged samples in each lot was determined. The results are shown in Table 12.

It is seen from Tables 11 and 12 that the storage period of Chinese noodles was prolonged by dipping them in a solution containing three ingredients, ethanol, trisodium phosphate and potassium carbonate as compared with the case of dipping it in a solution which contained only one or two of these three ingredients. This is considered to be due to the co-action of the antibacterial property of trisodium phosphate and the strength of the alkalinity by the carbonate, and to the synergistic effect of these by the conjoint use of ethanol with these salts.

The Chinese noodles in accordance with this invention were baked, and organoleptically examined. No change or abnormality was noted in their quality (taste, smell).

TABLE 11

| Test lot | | Concentrations of the ingredients of the dipping solution (wt. % as anhydrous substance) | | |
|---|---|---|---|---|
| | | Ethanol | Potassium carbonate | Trisodium phosphate |
| Control | (1) | (Not treated) | | |
| | (2) | 1.0 | | |
| | (3) | | 0.4 | 0.2 |
| | (4) | | 0.8 | |
| | (5) | | | 0.4 |
| | (6) | 1.0 | 0.8 | |
| | (7) | 1.0 | | 0.4 |
| Invention | (1) | 1.0 | 0.2 | 0.3 |
| | (2) | 1.0 | 0.4 | 0.2 |
| | (3) | 1.0 | 0.6 | 0.1 |

TABLE 12

| Test lot | | Storage period (days) | |
|---|---|---|---|
| | | Non-reheated noodles | Re-heated noodles |
| Control | (1) | 1.5 | 2.5 |
| | (2) | 2.0 | 4.0 |
| | (3) | 3.0 | 5.5 |
| | (4) | 2.5 | 5.0 |
| | (5) | 2.5 | 5.0 |
| | (6) | 5.0 | 8.5 |
| | (7) | 5.0 | 9.0 |
| Invention | (1) | 6.0 | 12.0 |
| | (2) | 6.0 | 12.0 |
| | (3) | 6.0 | 11.0 |

EXAMPLE 10

In this example, one dipping solution was repeatedly used for the dipping of Chinese noodles, and its effect was examined.

Steamed Chinese noodles were produced in the same way as in Example 9. One liter of a dipping solution in accordance with this invention (an aqueous solution containing 1.0% ethanol, 0.3% sodium carbonate and 0.22% tripotassium phosphate) and 1 liter of a control dipping solution (an aqueous solution containing 1% ethanol, and 0.44% potassium phosphate) were each used repeatedly 20 times for the dipping of 100 g of steamed Chinese noodles. The dipped Chinese noodles were then subjected to water removal, and treated in the same way as in Example 9. Their state of storage at 20° C. was examined. Ten milliliters of the dipping solution was sampled every time it was used five times, and its pH was measured by a pH meter. Furthermore, the amount of 1/100N hydrochloric acid required to neutralize the solution was measured, and defined as the degree of alkalinity.

The results are shown in Table 13. It is seen from the results that in dip-treating foods, the combination of alkali salts is important. When the dipping solution is repeatedly used for the dipping treatment of foods, the components of the foods and water adhering to the surface of the foods naturally migrate into the dipping solution to dilute its active components, and the amounts of the active components adhering to the foods gradually decrease. But when the three components (ethanol and two alkali salts, i.e. carbonate and alkali phosphate) are incorporated as in the dipping solution of this invention, the decrease of the pH of the dipping solution can be inhibited, and its alkalinity can be maintained high. As a result, the pH of the treated Chinese noodles increases. As a result, by the synergistic effect of the adhering alkali salts and ethanol, the growth of microorganism can be inhibited. According to such an external dipping method, it is frequently difficult to avoid a decrease in the concentrations of active ingredients unlike the case of incorporating such components in the material to be sterilized. But since the conjoint use of ethanol and an alkali carbonate and a trialkali phosphate inhibits the decrease of the concentrations of active ingredients, the dipping solution can be repeatedly used, and by the synergistic effect of the three ingredients, a very good practical effect can be obtained.

As is seen from Table 13, the storability of noodles treated with the dipping solution which has been used 16 to 20 times is reduced only by about 25 to 35% (both the non-reheated and reheated products) as compared with that of noodles treated with the dipping solution which has been used 1 to 5 times.

Boiled Chinese noodles also showed a marked storage effect in accordance with this invention by performing the same dipping treatment. No adverse effect on the quality of noodles was observed when the aqueous sterilizing agent of this invention was used.

stroyed without impairing the flavor or quality of the food which comes into contact with the sterilizing agent.

2. The method of claim 1 wherein the contact is maintained for a period of from about 30 seconds to about 30 minutes.

3. The method of claim 1 wherein the microorganisms comprises Escherichia coli NIHJ JC-2.

4. The method of claim 1 wherein the microorganism comprises bacteria of the genus Salmonella.

5. The method of claim 1 wherein the microorganism comprises coliform bacteria.

6. The method of claim 1 wherein the contact is effected by dipping the food contacting surface into the aqueous solution.

7. The method of claim 1 wherein the aqueous solution contains, per 100 parts of solution, 6.1 parts of ethanol, 2 parts of trisodium phosphate (12-hydrate) and 4 parts of sodium carbonate.

8. The method of claim 1 wherein the aqueous solution contains, per 100 parts of solution, 8.7 parts of ethanol, 1.7 parts of trisodium phosphate (12-hydrate) and 2 parts of sodium carbonate.

9. The method of claim 1 wherein the aqueous solution contains, per 100 parts of solution, 16 parts of ethanol, 6 parts of potassium carbonate and 6 parts of trisodium phsophate (12-hydrate).

10. The method of claim 1 wherein the aqueous solution contains, per 100 parts of solution, 10 parts of ethanol, 2 parts of sodium carbonate and 8 parts of anhydrous tripotassium phosphate.

11. The method of claim 1 wherein the aqueous solution contains, per 100 parts of solution, 10 parts of ethanol, 4 parts of potassium carbonate and 4 parts of anhydrous tripotassium phosphate.

12. The method of claim 1 wherein the aqueous solution contains, per 100 parts of solution, 5 parts of ethanol, 10 parts of anhydrous trisodium phosphate and 20 parts of potassium carbonate.

TABLE 13

| Test lot | | Dipping solution | | Steamed Chinese noodles | | Storage period (days) | |
|---|---|---|---|---|---|---|---|
| | | pH | Alkalinity | pH | Alkalinity | Non-reheated products | Reheated product |
| Invention | 0 | 11.85 | 50.0 | | | | |
| | 1–5 | 11.31 | 43.0 | 10.20 | 19.5 | 6.0 | 14.0 |
| | 6–10 | 11.05 | 37.5 | 10.07 | 18.0 | 6.0 | 12.0 |
| | 11–15 | 10.78 | 31.5 | 9.97 | 15.0 | 5.0 | 10.0 |
| | 16–20 | 10.48 | 26.5 | 9.91 | 14.0 | 4.5 | 9.0 |
| Control | 0 | 12.04 | 30.5 | | | | |
| | 1–5 | 11.27 | 26.0 | 10.16 | 14.5 | 5.0 | 12.0 |
| | 6–10 | 11.16 | 21.0 | 10.05 | 14.0 | 4.5 | 10.0 |
| | 11–20 | 10.86 | 17.0 | 9.83 | 12.5 | 4.0 | 7.0 |
| | 16–20 | 10.49 | 15.0 | 9.68 | 9.5 | 2.0 | 5.0 |
| Non-treated | | | | 9.50 | 6.3 | 1.5 | 2.5 |

What is claimed is:

1. A method of destroying microorganisms capable of spoiling food or causing food poisoning which comprises contacting surfaces which come into contact with food during the processing or handling thereof with an aqueous sterilizing agent having a pH of at least 10 and consisting essentially of an aqueous solution of about 0.5 to 75% by weight ethanol, an alkali carbonate selected from the group consisting of sodium carbonate and potassium carbonate, and a trialkali phosphate selected from the group consisting of trisodium phosphate and tripotassium phosphate, wherein the combined amount of carbonate and phosphate, on an anhydrous basis, is from about 0.5 to 40% by weight, for at least 30 seconds, whereby the microorganisms are effectively de- 13. A method of destroying microorganisms capable of spoiling food or causing food poisoning which comprises contacting the food with an aqueous sterilizing agent having a pH of at least 10 and consisting essentially of an aqueous solution of about 0.5 to 75% by weight ethanol, an alkali carbonate selected from the group consisting of sodium carbonate and potassium carbonate, and a trialkali phosphate selected from the group consisting of trisodium phosphate and tripotassium phosphate, wherein the combined amount of carbonate and phosphate, on an anhydrous basis, is from about 0.5 to 40% by weight, for at least 30 seconds, whereby the microorganisms are effectively destroyed without impairing the flavor or quality of the food which comes into contact with the sterilizing agent.

14. The method of claim 13 wherein the contact is maintained for a period of from about 30 seconds to about 30 minutes.

15. The method of claim 13 wherein the microorganisms comprises *Escherichia coli* NIHJ JC-2.

16. The method of claim 13 wherein the microorganism comprises bacteria of the genus Salmonella.

17. The method of claim 13 wherein the microorganism comprises coliform bacteria.

18. The method of claim 13 wherein the contact is effected by dipping the food into the aqueous solution.

19. The method of claim 13 wherein the aqueous solution contains, per 100 parts by weight of solution, 6.1 parts of ethanol, 2 parts of trisodium phosphate (12-hydrate) and 4 parts of sodium carbonate.

20. The method of claim 13 wherein the aqueous solution contains, per 100 parts by weight of solution, 8.7 parts of ethanol, 1.7 parts of trisodium phosphate (12-hydrate) and 2 parts of sodium carbonate.

21. The method of claim 13 wherein the aqueous solution contains, per 100 parts by weight of solution, 16 parts of ethanol, 6 parts of potassium carbonate and 6 parts of trisodium phosphate (12-hydrate).

22. The method of claim 13 wherein the aqueous solution contains, per 100 parts by weight of solution, 10 parts of ethanol, 2 parts of sodium carbonate and 8 parts of anhydrous tripotassium phosphate.

23. The method of claim 13 wherein the aqueous solution contains, per 100 parts by weight of solution, 10 parts of ethanol, 4 parts of potassium carbonate and 4 parts of anhydrous tripotassium phosphate.

24. The method of claim 13 wherein the aqueous solution contains, per 100 parts by weight of solution, 5 parts of ethanol, 10 parts of anhydrous trisodium phosphate and 20 parts of potassium carbonate.

25. An aqueous sterilizing agent capable of effectively eliminating food spoilage and food poisoning microorganisms associated with foods and the processing equipment and utensils which come into contact with foods, said agent being an aqueous composition having a pH of at least 10 and consisting essentially of an aqueous solution of about 0.5 to 75% by weight ethanol, an alkali carbonate selected from the group consisting of sodium carbonate and potassium carbonate and a trialkali phosphate selected from the group consisting of trisodium phosphate and tripotassium phosphate wherein the combined amount of the carbonate and phosphate, on an anhydrous basis, is about 0.5 to 40% by weight, said agent being capable of being maintained in contact with the food to be sterilized for at least 30 minutes without reducing the flavor or quality of the food.

26. The aqueous sterilizing agent of claim 25 which comprises, per 100 parts by weight of solution, 6.1 parts of ethanol, 2 parts of trisodium phosphate (12-hydrate) and 4 parts of sodium carbonate.

27. The aqueous sterilizing agent of claim 25 which comprises, per 100 parts by weight of solution, 8.7 parts of ethanol, 1.7 parts of trisodium phosphate (12-hydrate) and 2 parts of sodium carbonate.

28. The aqueous sterilizing agent of claim 25 which comprises, per 100 parts by weight of solution, 16 parts of ethanol, 6 parts of potassium carbonate and 6 parts of trisodium phosphate (12-hydrate).

29. The aqueous sterilizing agent of claim 25 which comprises, per 100 parts by weight of solution, 10 parts of ethanol, 2 parts of sodium carbonate and 8 parts of anhydrous tripotassium phosphate.

30. The aqueous sterilizing agent of claim 25 which comprises, per 100 parts by weight of solution, 10 parts of ethanol, 4 parts of potassium carbonate and 4 parts of anhydrous tripotassium phosphate.

31. The aqueous sterilizing agent of claim 25 which comprises, per 100 parts by weight of solution, 5 parts of ethanol, 10 parts of anhydrous trisodium phosphate and 20 parts of potassium carbonate.

32. The aqueous sterilizing agent of claim 25 which comprises, per 100 parts by weight of solution, about 7 parts ethanol, 2.5 to 4.0 parts sodium carbonate, and 0.5 to 10 parts trisodium phosphate (12-hydrate).

33. The aqueous sterilizing agent of claim 25 which comprises from about 15 to 40% by weight of ethanol, from about 0.05 to 0.2% by weight, in the anhydrous state, of trisodium phosphate, and from about 0.5 to 5% by weight of sodium carbonate.

34. The aqueous sterilizing agent of claim 25 which contains from about 15 to 40% by weight of ethanol, from about 0.5 to 5% of potassium carbonate, and from about 0.05' to 0.2% by weight in the anhydrous state of trisodium phosphate.

* * * * *